(12) United States Patent
Odom et al.

(10) Patent No.: US 6,738,720 B2
(45) Date of Patent: May 18, 2004

(54) APPARATUS AND METHODS FOR MEASUREMENT OF DENSITY OF MATERIALS USING A NEUTRON SOURCE AND TWO SPECTROMETERS

(75) Inventors: Richard C. Odom, Benbrook, TX (US); Robert D. Wilson, Fort Worth, TX (US)

(73) Assignee: Computalog U.S.A., Fort Worth, TX (US)

( * ) Notice: Subject to any disclaimer, the term of this patent is extended or adjusted under 35 U.S.C. 154(b) by 134 days.

(21) Appl. No.: 09/997,134

(22) Filed: Nov. 29, 2001

(65) Prior Publication Data

US 2003/0101011 A1 May 29, 2003

(51) Int. Cl.[7] ................................................. G01V 5/10
(52) U.S. Cl. .................................. 702/78; 702/6; 702/7; 702/8; 702/9; 702/11; 702/12; 702/13; 702/17
(58) Field of Search ................................. 702/6, 7, 8, 9, 702/11, 12, 13, 17, FOR 102; 250/252, 254, 256, 262, 264, 265, 266, 267, 268, 269.1, 269.2, 269.3, 269.4, 269.5, 270

(56) References Cited

U.S. PATENT DOCUMENTS

| | | | |
|---|---|---|---|
| 3,864,569 A | * | 2/1975 | Tittman ........................ 250/264 |
| 4,055,763 A | | 10/1977 | Antkiw |
| 4,122,339 A | * | 10/1978 | Smith et al. ................. 250/264 |
| 4,346,592 A | | 8/1982 | Fertl et al. |
| 4,471,435 A | * | 9/1984 | Meisner ........................... 702/8 |
| 4,503,328 A | | 3/1985 | Neufeld |
| 4,558,220 A | * | 12/1985 | Evans ........................ 250/269.3 |
| 4,583,397 A | | 4/1986 | Parma |
| 4,604,522 A | | 8/1986 | Arnold |
| 4,686,364 A | | 8/1987 | Herron |
| 4,746,801 A | | 5/1988 | Smith et al. |
| 4,810,876 A | | 3/1989 | Wraight et al. |
| 4,825,071 A | * | 4/1989 | Gadeken et al. ............ 250/256 |
| 5,021,653 A | | 6/1991 | Roscoe et al. |
| 5,053,620 A | | 10/1991 | McKeon et al. |
| 5,097,123 A | | 3/1992 | Grau et al. |
| 5,349,184 A | | 9/1994 | Wraight |
| 5,406,078 A | | 4/1995 | Jacobson |
| 5,440,118 A | | 8/1995 | Roscoe |
| 5,465,607 A | | 11/1995 | Corrigan et al. |
| 5,585,575 A | | 12/1996 | Corrigan et al. |
| 5,606,167 A | | 2/1997 | Miller |
| 5,659,169 A | * | 8/1997 | Mickael et al. ........... 250/269.3 |
| 5,767,510 A | * | 6/1998 | Evans ........................ 250/269.1 |
| 5,786,595 A | | 7/1998 | Herron et al. |
| 5,804,820 A | * | 9/1998 | Evans et al. ............... 250/269.6 |
| 5,821,541 A | * | 10/1998 | Tumer .................... 250/370.09 |
| 5,825,024 A | * | 10/1998 | Badruzzaman ........... 250/269.6 |
| RE36,012 E | * | 12/1998 | Loomis et al. ............ 250/259.4 |
| 5,910,654 A | * | 6/1999 | Becker et al. ............. 250/269.3 |
| 5,912,460 A | * | 6/1999 | Stoller et al. ............. 250/269.3 |
| 6,207,953 B1 | * | 3/2001 | Wilson ...................... 250/269.4 |
| 6,564,883 B2 | * | 5/2003 | Fredericks et al. ........... 175/50 |

* cited by examiner

Primary Examiner—Marc S. Hoff
Assistant Examiner—Carol S Tsai
(74) Attorney, Agent, or Firm—Patrick McCollum

(57) ABSTRACT

A system for measuring density of material which can be embodied to measuring bulk density of material penetrated by a borehole. The probe component of the system comprises a source of neutron radiation and preferably two gamma ray spectrometers. The neutron source induces gamma radiation with energies up to about 10 MeV within the material being measured. Formation bulk density is determined by combining spectra of the induced gamma radiation with preferably two gamma ray spectrometers at differing axial spacings from the source. The high energy and dispersed nature of the induced gamma radiation yields greater radial depth of investigation than that obtainable with prior art backscatter density systems, which typically use gamma ray sources local to a probe and of energy about 1.3 MeV or less. The system can alternately be embodied to measure other material properties and to measure density of materials not penetrated by a borehole.

29 Claims, 6 Drawing Sheets

APPARATUS AND METHODS FOR MEASUREMENT OF DENSITY OF MATERIALS USING A NEUTRON SOURCE AND TWO SPECTROMETERS

BACKGROUND OF THE INVENTION

1. Field of the Invention

This invention is directed toward measurement of density of material, and more particularly directed toward a system for measuring bulk density of material penetrated by a borehole, wherein the system comprises a source of neutron radiation and preferably two radiation detection spectrometers. The system can alternately be embodied to measure other material properties and to measure density of materials not penetrated by a borehole.

2. Background of the Art

Systems utilizing a source of radiation and a radiation detector have been used in the prior art for many years to measure density of material. One class of prior art density measuring systems is commonly referred to as "transmission" systems. A source of nuclear radiation is positioned on one side of material whose density is to be measured, and a detector which responds to the radiation is positioned on the opposite side. After appropriate system calibration, the intensity of measured radiation can be related to the bulk density of material intervening between the source and the detector. A second class of prior art density measuring systems is commonly referred to as "back scatter" systems. Both a source of nuclear radiation and a detector, which responds to the radiation, are positioned on a common side of material whose density is to be measured. Radiation impinges upon and interacts with the material, and a portion of the impinging radiation is scattered by the material and back into the detector. After appropriate system calibration, the intensity of detected scattered radiation can be related to the bulk density of the material.

Backscatter type systems have been used for decades to measure density of material, such as earth formation, penetrated by a borehole. The measuring instrument or "tool" typically comprises a source of radiation and at least one radiation detector which is axially aligned with the source and typically mounted within a pressure tight container.

Systems which employ the backscatter configuration with a source of gamma radiation and one or more gamma ray detectors are commonly referred to as "gamma-gamma" systems. Sources of gamma radiation are typically isotopic such as cesium-137 ($^{137}Cs$), which emits gamma radiation with energy of 0.66 million electron volts (MeV) with a half life of 30.17 years. Alternately, cobalt-60 ($^{60}Co$) is used as a source of 1.11 and 1.33 MeV gamma radiation with a half life of 5.27 years. The one or more gamma ray detectors can comprise ionization type detectors, or alternately scintillation type detectors if greater detector efficiency and delineation of the energy of measured scattered gamma radiation is desired.

The basic operational principles of prior art gamma-gamma type backscatter density measurement systems are summarized in the following paragraph. For purposes of discussion, it will be assumed that the system is embodied to measure the bulk density of material penetrated by a borehole, which is commonly referred to as a density logging system. It should be understood, however, that other backscatter density sensitive systems are known in the prior art. These systems include tools which use other types of radiation sources such as neutron sources, and other types of radiation detectors such as detectors which respond to neutron radiation or a combination of gamma radiation and neutron radiation.

A backscatter gamma-gamma density logging tool is conveyed along a well borehole penetrating typically earth formation. Gamma radiation from the source impinges upon material surrounding the borehole. This gamma radiation collides with electrons within the earth formation material and loses energy by means of several types of reaction. The most pertinent reaction in density measurement is the Compton scatter reaction. After undergoing typically multiple Compton scatters, a portion of the emitted gamma radiation is scattered back into the tool and detected by the gamma radiation detector. The number of Compton scatter collisions is a function of the electron density of the scattering material. Stated another way, the tool responds to electron density of the scattering earth formation material. Bulk density rather than electron density is usually the parameter of interest. Bulk density and electron density are related as $$\rho_e = \rho_b(2(\Sigma Z_i)/M\,W) \qquad (1)$$

where $\rho_e$=the electron density index;

$\rho_b$=the bulk density;

$(\Sigma Z_i)$=the sum of atomic numbers $Z_i$ of each element i in a molecule of the material; and MW=the molecular weight of the molecule of the material. For most materials within earth formations, the term $(2(\Sigma Z_i)/MW)$ is approximately equal to one. Therefore, electron density index $\rho_e$ to which the tool responds can be related to bulk density $\rho_b$, which is typically the parameter of interest, through the relationship $$\rho_b = A\rho_e + B \qquad (2)$$

where A and B are measured tool calibration constants. Equation (2) is a relation that accounts for the near linear (and small) change in average Z/A that occurs as material water fraction changes with material porosity, and hence changes with bulk density.

The radial sensitivity of the density measuring system is affected by several factors such as the energy of gamma radiation emitted by the source, the axial spacing between the source and one or more gamma ray detectors, and properties of the borehole and the formation. Formation in the immediate vicinity of the borehole is usually perturbed by the drilling process, and more specifically by drilling fluid "invades" the formation in the near borehole region. Furthermore, particulates from the drilling fluid tend to buildup on the borehole wall. This buildup is commonly referred to as "mudcake". Mudcake, invaded formation and other factors perturbing the near borehole region can adversely affect a formation bulk density measurement. It is of prime importance to maximize the radial depth of investigation of the tool in order to minimize the adverse effects of near borehole conditions. Generally speaking, an increase in axial spacing between the source and the one or more detectors increases radial depth of investigation. Increasing source to detector spacing, however, requires an increase in source intensity in order to maintain acceptable statistical precision of the measurement. Prior art systems also use multiple axial spaced detectors, and combine the responses of the detectors to "cancel" effects of the near borehole region. This method is marginally successful since nuclear systems are inherently shallow depth of investigation. Depth of investigation can be increased significantly by increasing the energy of the gamma-ray source. This permits deeper radial transport of gamma radiation into the formation. Unfortunately, there are no isotopic sources emitting gamma radiation above 1.33 MeV which have a half-life sufficiently long for typical commercial use and which are reasonably inexpensive to produce. Accelerator sources have been used in the prior art to generate gamma radiation of energy greater than 10 MeV. These sources are, however, physically large, costly to fabricate, costly to maintain, and often not suited for harsh environments such as a well borehole.

SUMMARY OF THE INVENTION

This invention is directed toward a system for measuring density and other properties of material penetrated by a borehole. Alternately, the system can be embodied for material analysis in a variety of non-borehole environments. Configuration of the system is based upon the backscatter concept discussed in the previous section of this disclosure.

The sensor instrument or "tool" comprises preferably an axially spaced source of radiation and preferably two axially spaced radiation detectors, which discriminate energy of radiation impinging upon the detectors.

The source is preferably a neutron source which emits, or induces within material being measured, gamma radiation with energy greater than energy obtainable with isotopic gamma ray sources. Further, the neutron-induced gamma source is dispersed within the material being measured, providing for a larger investigation depth than obtainable with prior art systems wherein a gamma ray source is located within a tool and not dispersed within material being measured. The dispersed source of gamma rays results from the reaction of transported neutrons with the materials surrounding the tool. The neutron source is preferably isotopic, although other types of radiation sources such as a neutron generator can be used. Conceptually, a source of gamma radiation can be used but an accelerator type gamma ray source would be required to obtain the desired high energy radiation. Furthermore, such a source has the disadvantage of being a point source outside of the material being measured rather than a dispersed gamma source within the material being measured.

A first suitable isotopic neutron source is americium 241-beryllium (AmBe), which produces alpha, gamma and neutron radiation. More specifically, the AmBe source produces gamma radiation at 4.43 MeV from the decay of carbon-12 ($^{12}C$), which is produced by alpha radiation from americium interacting with beryllium. Alternately, plutonium-beryllium (PuBe) can be used with similar results. Details of the alpha-beryllium reaction will be discussed in a subsequent section of this disclosure. The 4.43 MeV carbon gamma radiation is much more energetic that previously discussed gamma radiation from $^{137}Cs$ (0.66 MeV) and $^{60}Co$ (1.11 and 1.33 MeV). A gamma-gamma back scatter density measuring system using 4.43 MeV radiation will obtain much greater penetration into material being measured that that obtained with the prior art $^{137}Cs$ or $^{60}Co$ sources. More importantly, however, AmBe induces a source of gamma radiation within the material being measured resulting in a deeper depth of investigation. Neutrons from the AmBe source enters the material being measured. The neutron radiation produces gamma radiation primarily by inelastic scatter and thermal capture reactions with nuclei within the material. This neutron induced gamma radiation, and to a lesser proportion the back scattered 4.43 MeV gamma radiation, is detected by the preferably two axially spaced scintillation type gamma radiation spectrometers. The spectrometer positioned closest to the source is hereafter referred to as the "short spaced" detector, and the spectrometer positioned farthest from the source is hereafter referred to as the "long spaced" detector. Other types of detectors exhibiting spectral gamma ray response can be used. Alternate detectors include solid state detectors and gas filled detectors fabricated to be energy dependent.

A second suitable isotopic neutron source is Californium-252 ($^{252}Cf$). $^{252}Cf$ does not produce 4.43 MeV gamma radiation internally as does AmBe (and PuBe). Neutrons are, however, produced, enter the material being measured, and produce an (n–γ) radiation with energy spectral characteristics similar to the (n–γ) component generated by AmBe. Energies of a significant portion of the induced (n–γ) radiation are greater than energies obtainable with isotopic gamma ray sources. The induced gamma radiation is detected by the short spaced and the long spaced detectors. Fission gamma radiation is also produced and incorporated into the measurement.

The system embodied as a borehole device is conveyed along a borehole by means of a wireline or a drill string. Gamma ray spectra are measured in both long spaced and short spaced detectors. Spectra from each detector are split and integrated over preferably two energy regions or energy "windows". The energy windows are preferably contiguous, with a low energy window extending from a few hundred keV to about 3.0 MeV, and the high energy window extending from about 3.0 MeV to about 7 to 10 MeV. Energy windows for the short spaced and long spaced detectors are preferably identical, although different window limits can be employed using appropriate normalization methods. It should be understood that the energy limits of both the low window and the high window can be varied as long as the low energy window is responsive to down scatter gamma radiation and the high energy window is relatively insensitive to down scattered gamma radiation. As an example, a low energy window extending from several hundred keV to about 2 MeV would encompass a large percentage of down-scattered gamma radiation and backscatter radiation.

A normalization factor is next computed, wherein counts recorded in the high energy window of the long spaced detector multiplied by the normalization factor equals the counts recorded in the high energy window of the short spaced detector. Counts recorded in the low energy window of the long spaced detector are multiplied by the normalization factor thereby yielding a normalized low energy counts for the long spaced detector. The count measured in the low energy window of the short spaced detector is then subtracted from the normalized low energy count from the long spaced detector thereby yielding a low window count difference. For a given bulk density of material being measured, the percent of down scatter radiation increases with detector spacing. Furthermore, the percent of down scatter radiation is proportional the bulk density of the material being measured. These factors combine so that the low window count difference varies as a function of material bulk density, with low energy count difference increasing with increasing material bulk density. This process is recited mathematically in equations (1) and (2) discussed previously.

The functional relationship between low window count difference and material bulk density is determined by (1) calibrating by measuring tool response in materials of known density, or (2) by suitable tool response calculations such as Monte Carlo calculations, or (3) by a combination of measured and calculated tool responses.

BRIEF DESCRIPTION OF THE DRAWINGS

So that the manner in which the above recited features, advantages and objects of the present invention are obtained and can be understood in detail, more particular description of the invention, briefly summarized above, may be had by reference to the embodiments thereof which are illustrated in the appended drawings.

DETAILED DESCRIPTION OF THE PREFERRED EMBODIMENTS

This disclosure sets forth a system comprising apparatus and methods for measuring density and other properties of material. Other properties include material porosity and lithology.

The system can be embodied to measure properties of earth formation penetrated by a borehole. A measuring instrument or "tool" is conveyed within the borehole thereby measuring parameters of formation penetrated by the borehole. Properties are typically measured as a function of tool depth within the borehole thereby generating a "log" of the measured parameter. The tool can be conveyed by means of a wireline or a drill string. Alternately, the system can be embodied for material analysis in a variety of non-borehole environments. Configuration of the system is based upon the measure of back-scattered nuclear radiation as discussed conceptually in a previous section of this disclosure. Limitations of prior art backscatter systems are minimized using the present invention, as will become apparent in subsequent sections of this disclosure. Depth of investigation of the measurement is improved substantially by the dispersed nature of the gamma source as produced by neutron reactions in the surrounding materials. Investigation depth is also increased by the use of gamma radiation of energy higher than that available from common isotopic gamma-ray sources.

Figures 1, 2:
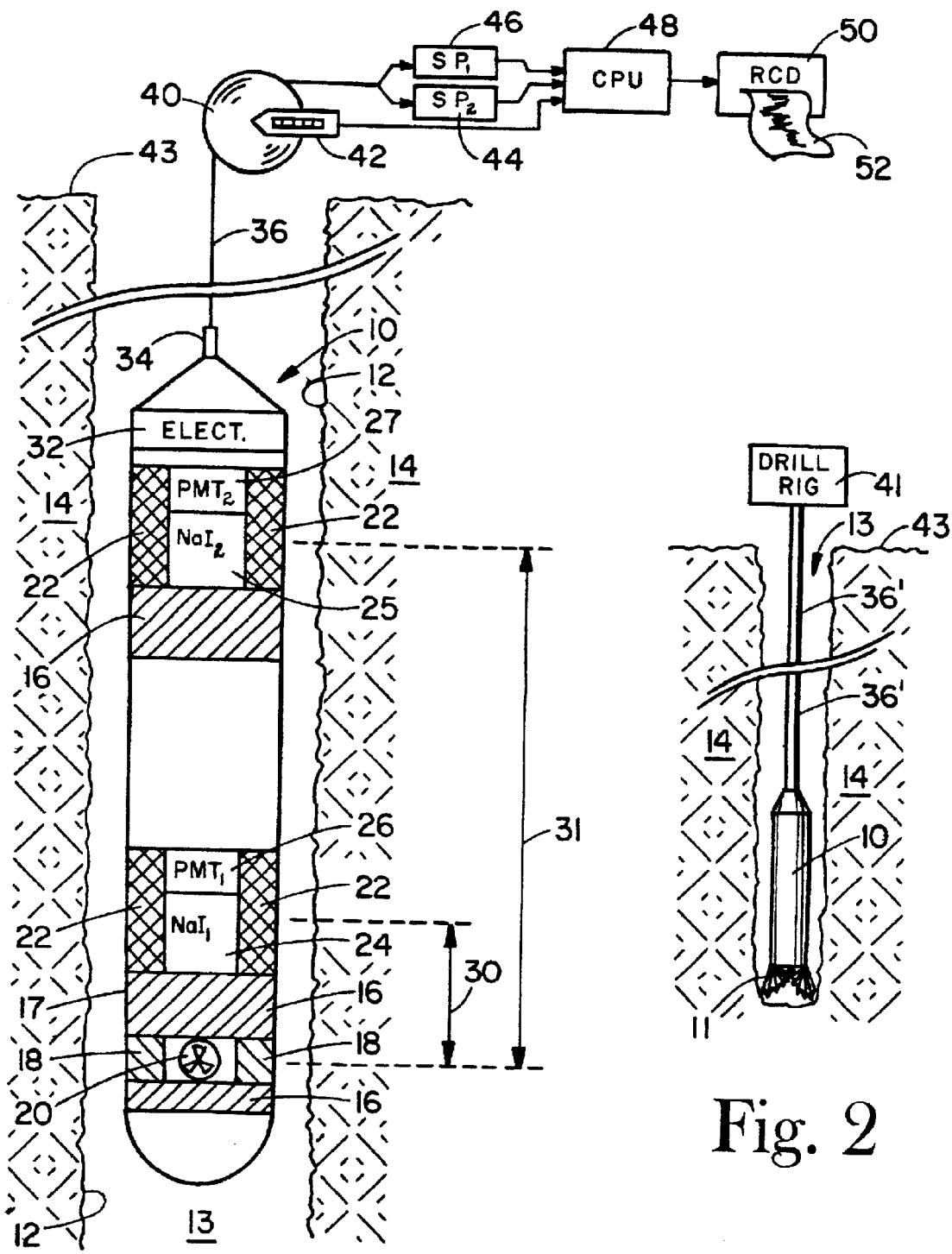
FIG. 1 illustrates the invention embodied as a wireline logging system.
FIG. 2 illustrates the invention embodied as a logging-while-drilling system.

FIG. 1 illustrates the invention embodied as a wireline well logging system. The system comprises a logging tool 10 connected to a wireline logging cable 36 by means of a connector 34. The tool 10 is shown suspended within a borehole 13 defined by a borehole wall 12 and penetrating an earth formation 14. The logging cable 36 passes over a sheave wheel 40 at the surface of the earth 43. A depth measuring means 42 cooperates with the sheave wheel 40 to generate a signal indicative of the depth of the tool 10 within the well borehole 13. Response signals from the tool 10 are processed by a first spectrometer processor 46 and a second spectrometer processor 44. Outputs from the first and second spectrometer processor 46 and 44 are input along with a signal from the depth measuring means 42 into a central processing unit (CPU) 48. Formation bulk density and other formation and borehole parameters of interest are computed within the CPU 48 and output to a recording means 50 which can comprise a digital memory, a digital recording means, or hard copy record as identified by the numeral 52.

Attention is now directed to the various elements of the tool 10 as shown in FIG. 1. The tool 10 comprises a source of radiation 20. The source 20 is preferably an isotopic neutron source such as Californium-252 ($^{252}$Cf), or alternately americium-beryllium (AmBe) which produces alpha, gamma and neutron radiation. The source 20 is surrounded by a fast neutron moderating material 18 such as high density polyethylene (HDPE) to maximize the thermal neutron flux entering the formation 14.

Americium emits alpha particles which react with Be to form $^{12}$C through the reaction $$^{9}Be(\alpha,n)^{12}C^* \tag{3}$$

thereby producing neutrons over a wide energy range. Excited $^{12}$C* decays to the ground state by the emission of 4.43 MeV gamma radiation.

$^{252}$Cf produces fast neutrons by spontaneous fission. Gamma rays are also produced by the spontaneous fission of $^{252}$Cf. The average neutron energy from $^{252}$Cf is about 2 MeV. The average gamma energy is about 0.7 MeV. The average energy of neutrons produced by an AmBe source from the Am ($\alpha$,n)Be reaction is about 4.5 MeV. In addition to differences in average energy, the neutron energy distribution of the two sources is significantly different. $^{252}$Cf neutrons are broadly peaked at about 1 MeV. Above about 2 MeV, neutron intensity decreases exponentially with increasing energy by about a factor of 10 every 3 MeV. On the other hand, AmBe neutrons exhibit several energy peaks in the range from a few hundred kilo electron volts (keV) to about 10 MeV. This energy distribution difference for the $^{252}$Cf and AmBe neutron sources results in differing formation neutron distributions for a given formation and borehole condition. These differing neutron distributions result in differing neutron induced gamma ray spectra. The fission gamma radiation is generally low in average energy and decreases in intensity with increasing energy. This fission gamma radiation can be effectively biased out by the setting of the lower limits of the low energy windows of the detectors.

A short spaced detector comprising a scintillation crystal 24 and a photomultiplier tube 26 is positioned a distance 30 from the source 20, and shielded from the source with a gamma ray and neutron shielding material 16 such as tungsten gammaloy. The shielding 16 minimizes neutron and gamma radiation from "streaming" directly from the source 20 into the scintillation crystal 24. Fast neutron moderating material 18 surrounds the source 20 to increase the flux of thermalized neutrons entering the formation 14. The scintillation crystal 24 is preferably sodium iodide (NaI), but other scintillation crystal materials can be used. The scintillation crystal 24 is radially shielded with a material 22 which readily absorbs thermal neutrons impinging thereon thereby preventing thermal neutron activation and capture reactions from occurring within the scintillation crystal. A suitable material for the shielding material 22 is HDPE, which moderates fast neutrons, and including additives such as Cd, Gd and B which are all prolific thermal neutron absorbing elements.

Still referring to FIG. 1, a long spaced detector comprising a scintillation crystal 25 and photomultiplier tube 27 and which is axially spaced from the source 20 by a distance 31. Neutron and gamma ray shielding 16 are disposed between short spaced and the long spaced detectors. The spacings 30 and 31 are preferably about 7 inches and 14 inches, respectively. These spacings are based on laboratory measurements. The long spacing is preferably greater than 14 inches for better density sensitivity, but will be limited by source strength and corresponding count rate statistics considerations. The shielding-spacing arrangement minimizes response of the short and long spaced detectors to direct flux from the source 20, and also maximizes the desired signal related to formation bulk density as will be discussed in a subsequent section of this disclosure. It is preferred that the long and short spaced detectors be identical in response characteristics to facilitate normalization, which will be discussed in a subsequent section of this disclosure. Alternately, different long and short spaced detector responses can be incorporated using appropriate response normalization methods. All elements of the tool 10 are mounted within a pressure housing 17, and powered and controlled by an electronics package 32.

FIG. 2 illustrates conceptually the tool 10 embodied as a logging-while-drilling (LWD) system. The tool 10 is conveyed by a drill string 36' along the borehole 13 penetrating the formation 14. A drill bit 11 terminates the drill string 36'. Surface drilling and recording apparatus are well known in the LWD art, and are therefore illustrated conceptually at 41 for brevity.

Embodied either as a wireline or LWD system, neutrons and gamma radiation from the source 20 enter the formation 14. The neutron radiation produces gamma radiation by inelastic scatter and thermal capture reactions with nuclei within the formation 14. A portion of the neutron induced radiation is down scattered as it is transported through the formation 14 and impinges upon the long and short spaced detectors.

Figure 3A:
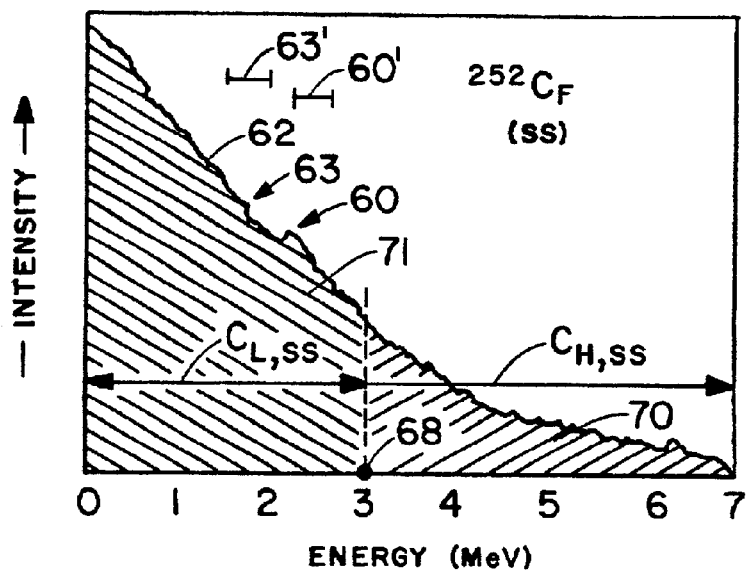
FIG. 3a is a gamma ray spectrum measured with the short spaced detector using $^{252}$Cf as a source of radiation.

FIG. 3a is a spectrum 62 of gamma ray intensity plotted as a function of gamma ray energy as measured by the short spaced detector using $^{252}$Cf as a source 20. The peak 60 at 2.23 MeV is produced by thermal capture of neutrons by hydrogen. The peak at 63 is produced by inelastic scatter of fast neutrons by the element silicon (Si). Measures of counts in these peaks can be related to other parameters of the material being measured as will be discussed in subsequent sections of this disclosure. These and other peaks are superimposed on a substantial and complex distribution of inelastic scatter and capture gamma radiation induced by neutrons from the source 20 interacting with nuclei within the formation 14. The spectrum is partitioned into two continuous low and high energy windows. A low energy window extends from gamma ray energy of a few hundred keV to an energy of about 3.0 MeV, and is designated by the numeral 68. An alternate upper energy of about 2 MeV (not shown) can be used to exclude any unscattered 2.223 MeV hydrogen thermal capture gamma radiation. A high energy window extends from about 3.0 MeV to an energy of about 7.0 MeV or greater. Counts recorded within the low energy window are identified by the shaded area 71 and are hereafter designated as $C_{L,SS}$, where the "L" identifies the low energy window and "SS" identifies the short spaced detector. Counts recorded within the high energy window are identified by the shaded area 70 and hereafter designated as $C_{H,SS}$, where the "H" identifies the high energy window and "SS" again identifies the short spaced detector. Counts in the peaks 60 and 63 can be obtained by measuring counts in the energy windows 60' and 63', respectively, or by other methods such as spectrum stripping.

Figure 3B:
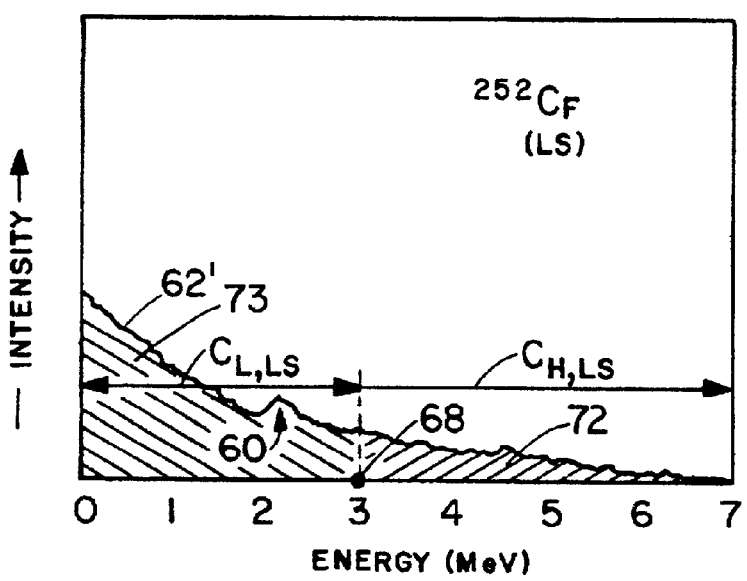
FIG. 3b is a gamma ray spectrum measured with the long spaced detector using $^{252}$Cf as a source of radiation.

FIG. 3b is a spectrum 62' of gamma ray intensity plotted as a function of gamma ray energy as measured by the long spaced detector using $^{252}$Cf as a source 20. The peak 60 again identifies the 2.223 MeV gamma ray produced by thermal capture of neutrons by hydrogen, which again is superimposed on a substantial and complex distribution of inelastic scatter and capture gamma radiation induced by neutrons from the source 20 interacting with nuclei within the formation 14. The spectrum 62' is lower in intensity than the short spaced detector spectrum 62 shown in FIG. 3a due to a greater source-detector spacing 31. The long spaced detector spectrum 62' is partitioned once again into two continuous low and high energy windows extending from near a few hundred keV to 3.0 MeV and 3.0 MeV to about 7.0 MeV or larger, respectively. Counts recorded within the low energy window are identified by the shaded area 73 and are hereafter designated as $C_{L,LS}$, where the "L" identifies the low energy window and "LS" identifies the long spaced detector. Counts recorded within the high energy window are identified by the shaded area 72 and are hereafter designated as $C_{H,LS}$, where the "H" identifies the high energy window and "LS" again identifies the long spaced detector.

A normalization factor is next computed from the relationship $$N = C_{H,SS}/C_{H,LS} \quad (4)$$

where $C_{H,SS}$ and $C_{H,LS}$ have been defined previously. Physically, equation (4) normalizes the long spaced and short spaced detectors to counts recorded in their high energy windows. Counts recorded in the low energy window of the long spaced detector, $C_{L,LS}$, are multiplied by the normalization factor N thereby yielding a normalized low energy count for the long spaced detector which is $$C'_{L,LS} = NC_{L,LS} \quad (5)$$

The count measured in the low energy window of the short spaced detector, $C_{L,SS}$, is then subtracted from the normalized low energy count for the long spaced detector, $C'_{L,LS}$, thereby yielding a low window count difference $$\Delta C = C'_{L,LS} - C_{L,SS} \quad (6)$$

For a given bulk density of material being measured, the percent of down scatter radiation increases with detector spacing. Stated another way, percent down scatter is greater in the long spaced detector. Furthermore, the percent of down scatter radiation is proportional the bulk density of the material being measured. Both the proportional relationship between Compton scattering and electron density, and the near proportionality of electron density and bulk density, have been discussed in detail in previous sections of this disclosure. These factors combine so that the low window count difference varies as a function of material bulk density, with low energy count difference increasing with increasing material bulk density. This effect is illustrated graphically in FIG. 4a, which is a plot of low window count difference, ΔC', as a function of gamma ray energy increments or energy "channels", with $^{252}$Cf as a source 20. Curve 76 is a spectrum measured in a silicate formation (gabbro) with bulk density $\rho_b$=3.01 grams per cubic centimeter (gm/cm$^3$).

Curve 78 is a spectrum measured in a silicate formation (sandstone) with bulk density $\rho_b$=2.01 gm/cm 3. Because of the normalization procedure discussed above, curves 76 and 78 above the energy 66 (high energy window) essentially overlay at a value of ΔC'=0 as identified at 80. Below the energy 66 (low energy window), the curves deviate with curve 76 representing the more dense material being larger.

The functional relationship $f(K_i, \Delta C)$ between low window count difference ΔC and material bulk density ρb is defined as $$\Lambda_b = f(K_i, \Delta C) \quad (7)$$

where ΔC is the sum of values ΔC' over a given energy window and where $K_i$ are tool calibration constants determined by (1) measuring tool response in materials of known density, or (2) by suitable tool response calculations such as Monte Carlo calculations, or (3) by a combination of measured and calculated tool responses. The relationship between the quantity of interest $\rho_b$ and the quantity ΔC computed from measured quantities is shown conceptually in FIG. 5, with $f(K_i, \Delta C)$ being represented by a curve 82 when $^{252}$Cf is used as a neutron source 20.

Figure 3C:
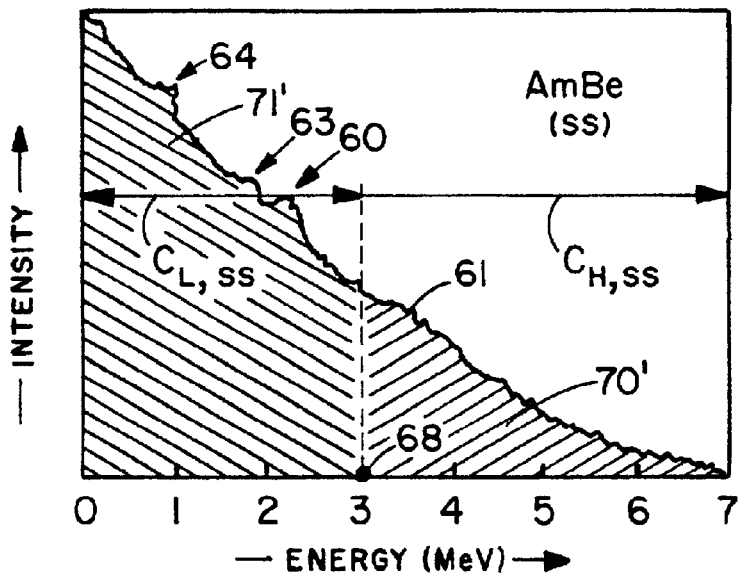
FIG. 3c is a gamma ray spectrum measured with the short spaced detector using AmBe as a source of radiation.

As mentioned previously, AmBe is an alternative source 20. FIG. 3c is a spectrum 61 of gamma ray intensity plotted as a function of gamma ray energy for gamma radiation measured by the short spaced detector. AmBe is used as a source 20. The peak 60 at 2.23 MeV is again produced by thermal capture of neutrons by hydrogen, the peak 63 at 1.78 MeV is produced by inelastic scatter of neutrons from Si, and the peak 64 at 0.85 MeV is produced by the inelastic scatter of neutrons from iron (Fe). All peaks are superimposed on a substantial and complex distribution of inelastic scatter and capture gamma radiation induced by neutrons from the AmBe source 20 interacting with nuclei within the formation 14. As discussed in the section using 252Cf as a source, the spectrum is partitioned into two contiguous low and high energy windows with energy ranges defined previously. Counts recorded within the low energy window are identified by the shaded area 71' and again designated as $C_{L,SS}$. Counts recorded within the high energy window are identified by the shaded area 70' and again designated as $C_{H,SS}$.

Figure 3D:
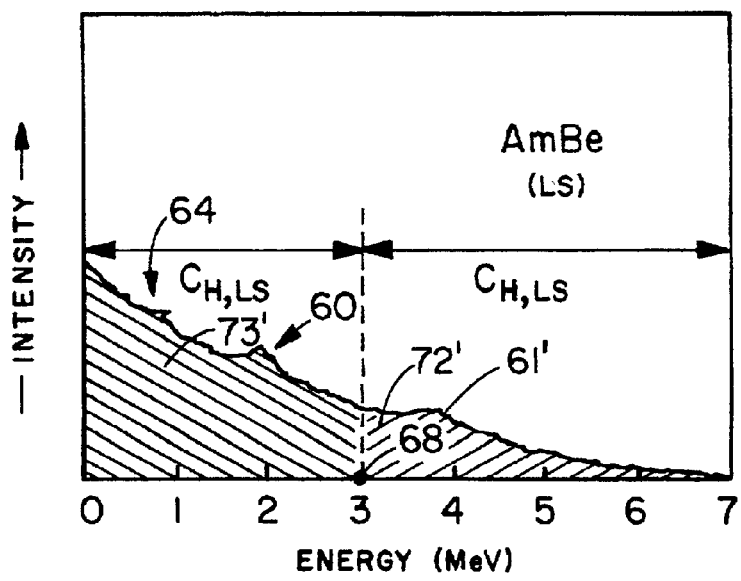
FIG. 3d is a gamma ray spectrum measured with the long spaced detector using AmBe as a source of radiation.

FIG. 3d is a spectrum 61' of gamma ray intensity plotted as a function of gamma ray energy for gamma radiation measured by the long spaced detector using AmBe as a source 20. The peak structure is the same as that in the short spaced detector spectrum 61 shown in FIG. 3c, but the long spaced detector spectrum 61' is again lower in intensity than the short spaced detector spectrum due to a greater source-detector spacing 31. Previously discussed peaks 60 and 64 from Fe and Si are somewhat less pronounced. The long spaced detector spectrum 61' is partitioned once again into two contiguous low and high energy windows. Counts recorded within the low energy window are identified by the shaded area 73' and are again designated as $C_{L,LS}$. Counts recorded within the high energy window are identified by the shaded area 72' and again designated as $C_{H,LS}$.

Figure 4B:
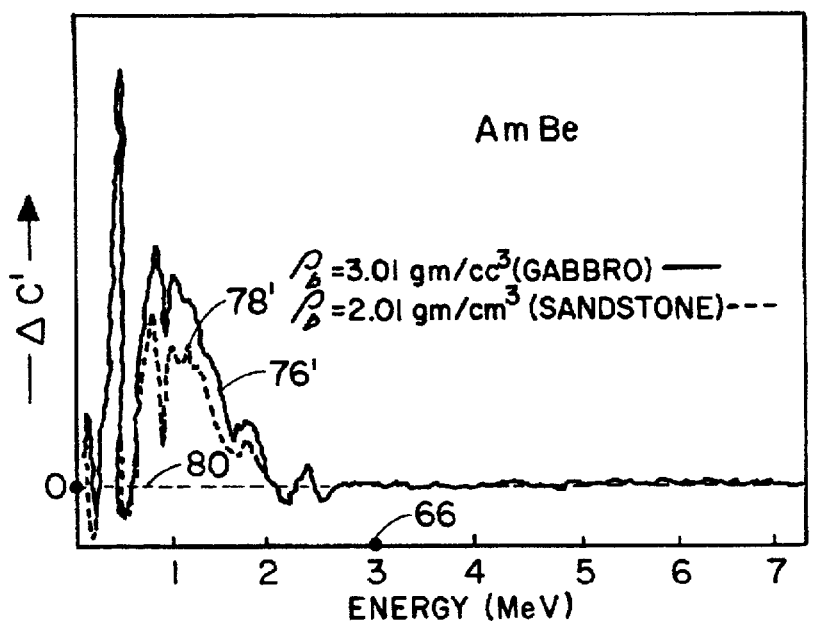
FIG. 4b is a plot of low window count difference as a function of gamma ray energy for differing density material and using AmBe as a source of radiation.
Figure 4A:
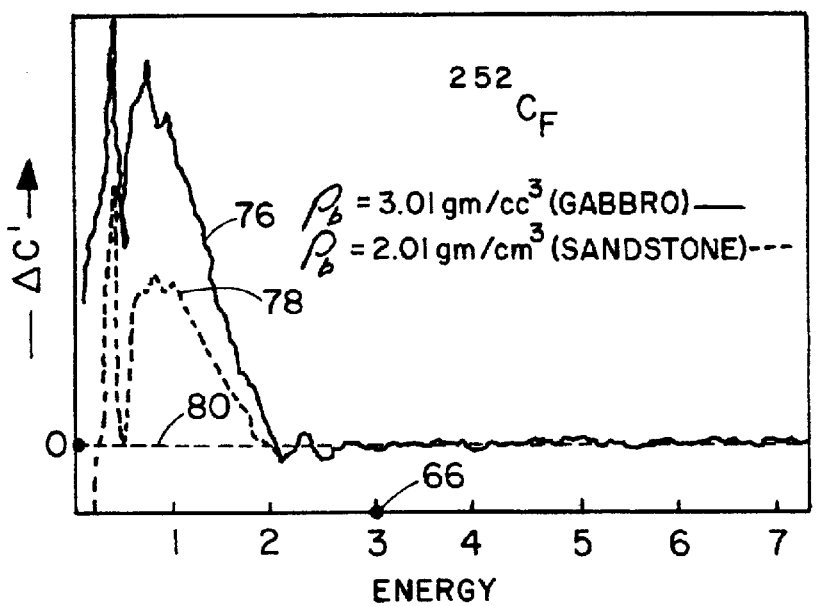
FIG. 4a is a plot of low window count difference as a function of gamma ray energy for differing density material and using $^{252}$Cf as a source of radiation.

The quantities N, $C'_{L,LS}$ and ΔC using AmBe as a source 20 are again computed using equations (4), (5) and (6), respectively. FIG. 4b is a plot of low window count difference, ΔC', as a function of gamma ray energy "channels", with AmBe as a source 20. Curve 76' is a spectrum measured in the silicate formation with bulk density $\rho_b$=3.01 gm/cm$^3$. Curve 78' is a spectrum measured in the silicate formation with bulk density $\rho_b$=2.01 gm/cm$^3$. As in FIG. 4a, the normalization procedure is such that curves 76' and 78' above the energy 66 (high energy window) essentially overlay at a value ΔC'=0 as identified at 80. Below the energy 66 (low energy window), the curves deviate with curve 76' representing the more dense material being larger. It should be noted, however, that deviation or "spread" between curves 76' and 78' is not as great as deviation between curves 76 and 78 shown in FIG. 4a. The functional relationship $f(K_i, \Delta C)$ between $\rho_b$ and ΔC, for AmBe as a source, is shown conceptually as curve 82' in FIG. 5. As previously defined, ΔC is the sum of values ΔC' over a specific energy window. Physically, the values of $K_i$ are such that $f(K_i, \Delta C)$ is not as sensitive to ΔC as a function of $\rho_b$ when AmBe is used as a source. This indicates that, for a given tool geometry, $^{252}$Cf is the preferred source 20 for the tool 10.

The preference of a $^{252}$Cf source is further illustrated in the following tables. Tabulated counts are measured in known test formations and are tabulated in count rates in counts per second. Table 1 is a tabulation of all measured and computed parameters discussed above in formations of 2.01 gm/cm$^3$ and 3.01 gm/cm$^3$ using $^{252}$Cf as a source. Note that the difference or "spread" in ΔC between the two formations is $\Delta C_{3.01} - \Delta C_{2.01}$=1397 counts per second with an average deviation of 281 counts per second.

TABLE 1

Source: $^{252}$Cf

| N | $\rho_b$ | $C_{L,SS}$ | $C_{L,LS}$ | $C_{H,SS}$ | $C_{H,LS}$ | $C'_{L,LS}$ | ΔC |
|---|---|---|---|---|---|---|---|
| 4.999 | 2.01 | 6588 | 1447 | 614 | 123 | 7238 | 650 |
| 6.980 | 3.01 | 7323 | 1342 | 698 | 100 | 698 | 2046 |

$\Delta C_{3.01} - \Delta C_{2.01} = 1397$
Average deviation = 281
Percent deviation = 20%

Table 2 is a tabulation of all measured and computed parameters discussed above in formations of 2.01 gm/cm$^3$ and 3.01 gm/cm$^3$ using AmBe as a source. Note that the difference or "spread" in ΔC between the two formations is $\Delta C_{3.01} - \Delta C_{2.01}$=735 counts per second with an average deviation of 362 counts per second.

TABLE 2

Source: AmBe

| N | $\rho_b$ | $C_{L,SS}$ | $C_{L,LS}$ | $C_{H,SS}$ | $C_{H,LS}$ | $C'_{L,LS}$ | ΔC |
|---|---|---|---|---|---|---|---|
| 5.652 | 2.01 | 12766 | 2417 | 1254 | 222 | 13659 | 894 |
| 7.184 | 3.01 | 14859 | 2295 | 1454 | 202 | 16487 | 1629 |

$\Delta C_{3.01} - \Delta C_{2.01} = 735$
Average deviation = 362
Percent deviation = 49%

In comparing data listed in Tables 1 and 2, it is apparent that the sensitivity of the bulk density measurement, the average deviation, and a corresponding percent average deviation, are all superior using $^{252}$Cf as a source. Stated another way, the $^{252}$Cf source yields a more sensitive measurement with less statistical uncertainty. As discussed previously, the superiority of the $^{252}$Cf source can also be seen graphically in comparing FIGS. 4a and 4b.

Figure 5:
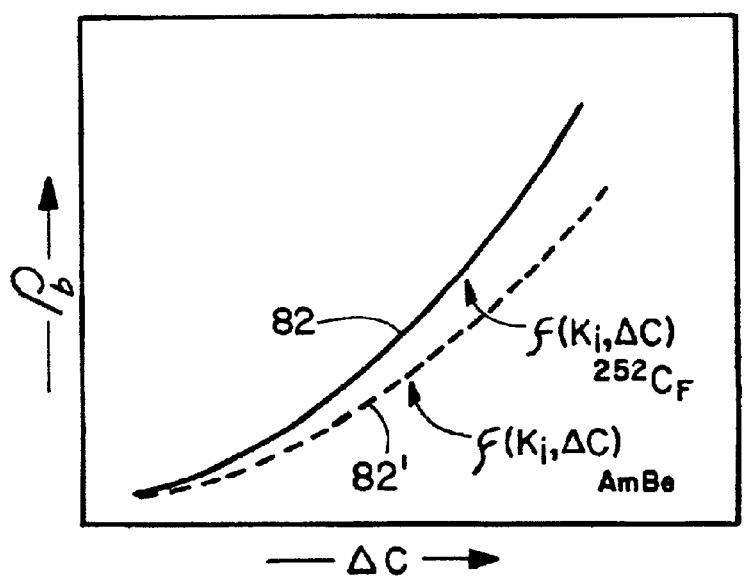
FIG. 5 is a conceptual representation of the functional relationship between low window count difference and bulk density for $^{252}$Cf and AmBe sources.

Calibration curves 82 and 82' depicted in FIG. 5 are typically for a specific lithology such as silicates or calcites. In order to maximize the accuracy of the formation bulk density measurement, some knowledge of formation lithology is required. This information can be obtained from additional types of measurements using, as examples, acoustic or electromagnetic systems. Lithology information can also be extracted from the response of the present invention.

Thermal capture or inelastic scatter gamma radiation from identifying elements of formation lithology can usually be identified and measured in the spectra recorded by the short spaced and long spaced detectors. As an example, characteristic radiation from elemental silicon as shown in the peak 63 of FIGS. 3a and 3c can be used to identify the material being measured as containing silicates, and to quantify the amount of silicate from counts recorded in the energy window 63'. A measure of counts in one or more peaks from calcium (not shown) can be used to identify the lithology of the material being measured as a calcite. Additional energy windows, or other techniques such as spectrum fitting, can be used to quantify this characteristic radiation which is subsequently used to determine lithology. Corrections for formation lithology can be made directly in the data processing methodology.

It is noted that the amount of hydrogen contained within the material being measured can be obtained from the magnitude of counts in the peak 60 using the energy window 60'. If other material parameters are known, such as the type of liquid saturating pores pace of the material, the porosity of the material can be obtained from a measure of hydrogen content.

Figure 6:
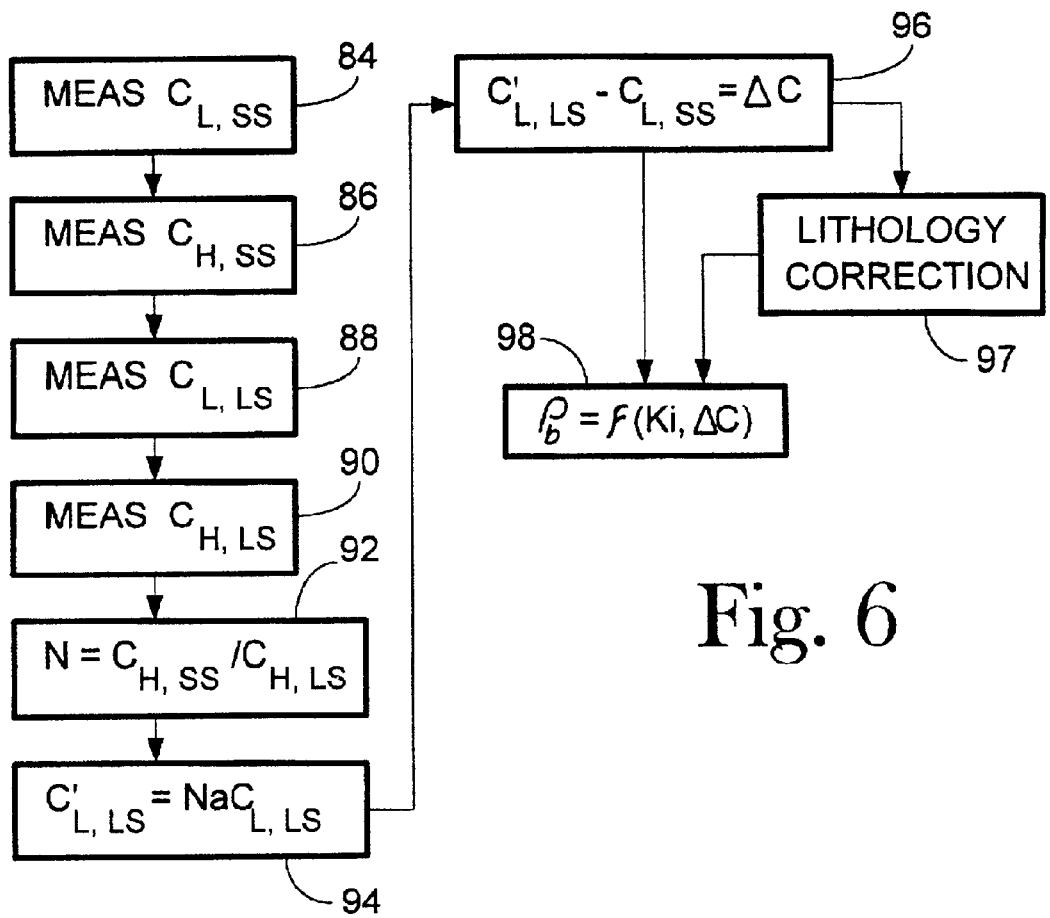
FIG. 6 is a flow chart of the data processing method.

The data processing methodology is summarized in the flow chart of FIG. 6. The process works equally well for data measured using AmBe or $^{252}$Cf as a neutron source. Parameters $C_{L,SS}$, $C_{L,LS}$, $C_{H,SS}$, and $C_{H,LS}$ are measured at steps 84, 88, 86 and 90, respectively. The normalization factor N is computed at step 92. The normalized low energy window count for the long spaced detector, $C'_{L,LS}$, is computed at step 94. The parameter $\Delta C$ is computed at step 96. An optional lithology correction, using elemental concentration measurements of the material, is made at step 97, and $\Delta C$ is converted to bulk density $\rho_b$ at step 98.

The CPU 48 illustrated in FIG. 1 is programmed to perform computations to convert measured quantities $C_{L,SS}$, $C_{L,LS}$, $C_{H,SS}$, and $C_{H,LS}$, and optionally lithology measurements and corrections, into one or more parameters of interest such as bulk density $\rho_b$. Computations are summarized in the flow chart of FIG. 6. It should be understood by those of ordinary skill in the art that the mathematical algorithms illustrated and discussed above represent one method for the conversion of measured or computed parameters into one or more parameters of interest. Other algorithms and methodology can be developed to obtain similar results. As an example, other normalization techniques can be used to normalize long and short spaced detector responses if high and low energy windows differ in energy range. Furthermore, the high and low windows can be separated or even overlapped. Differing long and short spaced detector sensitivities will also require modifications in the normalization process. The response of the system to changes in density can be reflected in other combinations of data, such as the ratio $C'_{L,LS}/C_{L,SS}$ instead of the difference $C'_{L,LS}-C_{L,SS}$. The functional relationship between measured parameters, computed parameters, and formation parameters of interest can, however, be effectively determined using algorithms specifically set forth in this disclosure.

Figure 7:
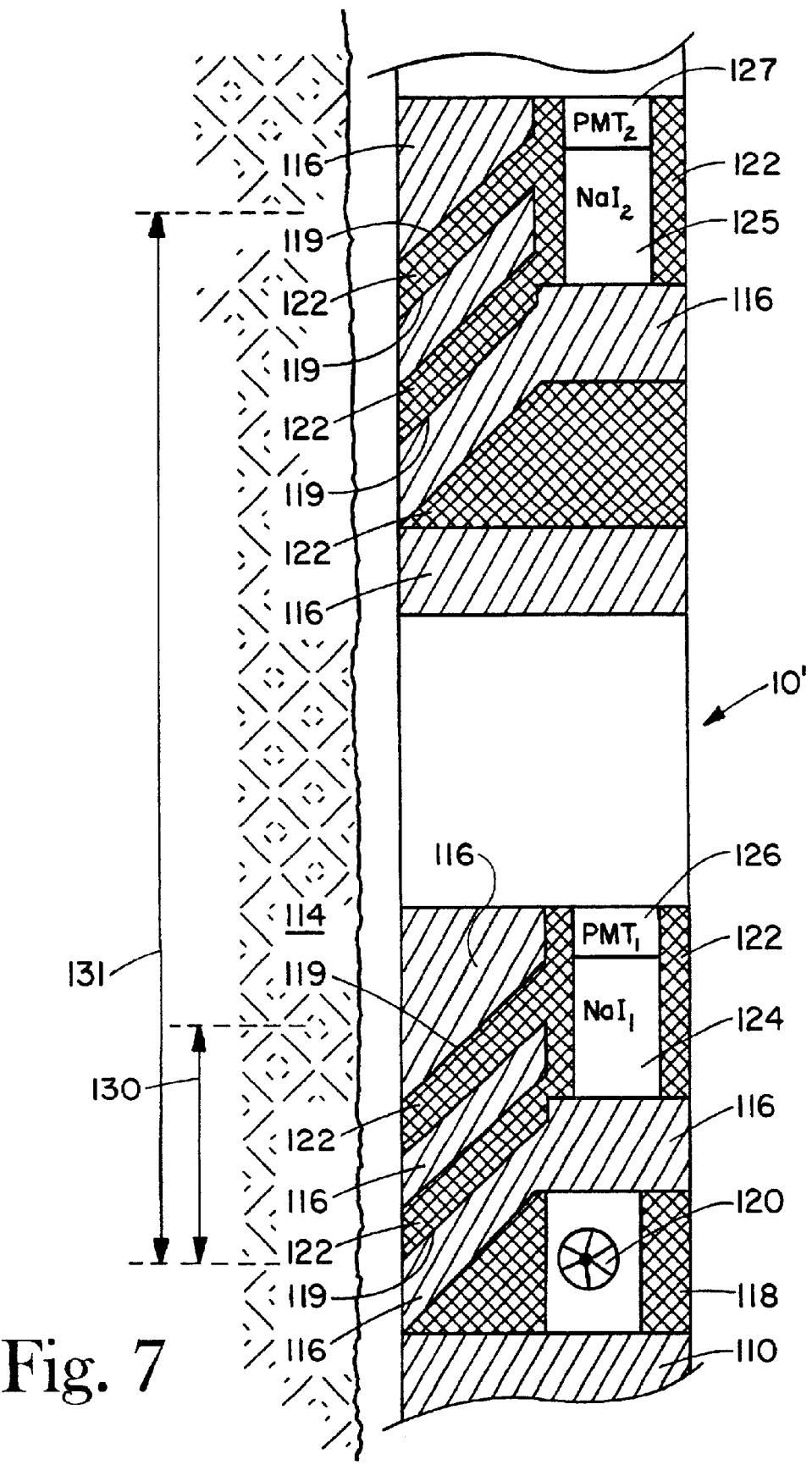
FIG. 7 depicts the invention embodied to measure material bulk density and other material properties in a non-borehole geometry.

The invention can be embodied with a non-borehole tool 10' as shown in FIG. 7. The tool 10' comprises a source of radiation 120, which is displaced radially from the major axis of the tool. The source 120 is again preferably $^{252}$Cf and is surrounded by a fast neutron moderating material 118. A short spaced detector comprising a scintillation crystal 124 and a photomultiplier tube 126 is axially spaced at a distance 130 from the source 120, and is shielded with a gamma ray and neutron shielding material 116 such as tungsten gammaloy. As in the borehole embodiment, the shielding 116 minimizes neutron and gamma radiation from "streaming" directly from the source 120 into the scintillation crystal 124. The fast neutron moderating material 118 surrounds the source 120 to increase the flux of thermalized neutrons entering the material 114 to be measured. The scintillation crystal is preferably sodium iodide (NaI), but other scintillation crystal materials can be used. The scintillation crystal 124 is radially shielded with a material 122 which readily absorbs thermal neutrons impinging thereon thereby preventing thermal neutron activation and capture reactions from occurring within the scintillation crystal 124. A suitable material for the shielding material 122 is again HDPE, which moderates fast neutrons plus additives such as Cd, Gd and B which are all prolific thermal neutron absorbing elements.

Still referring to FIG. 7, a long spaced detector comprising a scintillation crystal 125 and photomultiplier tube 127 are axially spaced at a distance 131 from the source 120. Neutron and gamma ray shielding 116 is disposed between the long and short spaced detectors. As in the borehole embodiment shown in FIG. 1, it is preferred that the first and second scintillation detectors be identical in response characteristics to facilitate spectral normalization. Both the short and long spaced detectors are displaced radially from the major axis of the tool 10'.

The tool 10' is positioned against or near the material 114 to be measured as shown in FIG. 7. Between the long and short spaced detectors and the material 114 to be measured, the gamma ray and neutron shielding material 116 is fabricated to form angled collimation conduits defined by the walls 119. The collimator conduits are filled with thermal neutron shielding material 122. This enhances sensitivity to Compton scatter radiation by collimating the scintillators to preferred angles of scatter. Furthermore, the radial displacement of the two source-scintillator pairs away from the material 114 being measured allows the thickness of material between the pairs and the material to be maximized for a given radial dimension of the tool 10'.

Data collection methods, processing methods and auxiliary equipment for the system embodied as shown in FIG. 7 are the same as those for the system embodied as shown in FIG. 1 and in FIG. 2.

To summarize, the bulk density measuring system utilizing neutron-induced high energy gamma radiation which is dispersed within the measured material provides an increased depth of investigation when compared with prior art systems using lower energy isotopic gamma-ray sources localized to the tool. This increased depth of investigation is obtained without necessitating the use of an accelerator source, which is costly to fabricate, costly to maintain, and operationally unreliable when compared to "chemical" or isotopic neutron sources. In addition, the system generates inelastic scatter, thermal neutron capture, and elemental activation gamma radiation which can be used to determine a variety of other material properties such as elemental concentrations, lithology, porosity and the like.

While the foregoing disclosure is directed toward the preferred embodiments of the invention, the scope of the invention is defined by the claims, which follow.

What is claimed is:

1. A method for determining a property of a material, comprising the steps of:
   (a) inducing, within said material, gamma radiation comprising energies greater than about 3 MeV;
   (b) measuring a first gamma ray spectrum and a second gamma ray spectrum resulting from said induced gamma radiation;

(c) normalizing said first and said second gamma ray spectrum in a first energy region;
(d) measuring down scatter gamma radiation in a second energy region of said normalized first and second gamma ray spectra; and
(e) determining said property from said measure of down scatter radiation.

2. The method of claim 1 comprising the additional step of forming said induced gamma radiation by means of a neutron source.

3. The method of claim 2 wherein:
(a) said first gamma ray spectrum is measured at a first distance from said neutron source;
(b) said second gamma ray spectrum is measured at a second distance from said neutron source wherein said second distance is greater than said first distance;
(c) said first energy region comprises gamma radiation with energy greater than gamma radiation in said second energy region;
(d) said second gamma ray spectrum is normalized to said first gamma ray spectrum thereby forming a normalized second gamma ray spectrum; and
(e) said property is determined from a difference in said down scatter radiation in said second energy regions of said first gamma ray spectrum and said normalized second gamma ray spectrum.

4. The method of claim 1 wherein said property is bulk density.

5. The method of claim 1 wherein said material is earth formation penetrated by a borehole.

6. The method of claim 5 comprising the additional step of measuring said property as a function of depth within said borehole by conveyance of apparatus along said borehole by means of a wireline.

7. The method of claim 5 comprising the additional step of measuring said property as a function of depth within said borehole by conveyance of apparatus along said borehole by means of a drill string.

8. A method for determining a property of a material, comprising the steps of:
(a) inducing gamma radiation within said material by means of a neutron source;
(b) measuring a first gamma ray spectrum resulting from said induced gamma radiation at a first spacing from said neutron source;
(c) measuring a second gamma ray spectrum resulting from said induced gamma radiation at a second spacing;
(d) normalizing said second gamma ray spectrum to said first gamma ray spectrum in a first energy region thereby creating a normalized second gamma ray spectrum; and
(e) combining said first gamma ray spectrum with said normalized second gamma ray spectrum in a second energy region to determine a measure of said property.

9. The method of claim 8 wherein said second spacing is greater than said first spacing.

10. The method of claim 9 wherein:
(a) said first energy region ranges from about 3 MeV to about 7 MeV; and
(b) said second energy region ranges from about several hundred keV to about 3 MeV.

11. The method of claim 8 wherein said first gamma ray spectrum in said second energy region is subtracted from said normalized second gamma ray spectrum in a second energy region to determine said measure of said property.

12. The method of claim 8 wherein said neutron source comprises Californium-252.

13. The method of claim 8 wherein said property is bulk density.

14. The method of claim 13 comprising the additional steps of:
(a) identifying one or more elements within said material from said first gamma ray spectrum and said second gamma ray spectrum;
(b) determining lithology of said material from said one or more elements; and
(c) correcting said measure of bulk density for effects of said lithology of said material.

15. The method of claim 8 wherein said material is earth formation penetrated by a borehole.

16. The method of claim 15 comprising the additional step of conveying apparatus used to obtain said measure of said property within said borehole by means of a wireline.

17. The method of claim 15 comprising the additional step of conveying apparatus used to obtain said measure of said property within said borehole by means of a drill string.

18. An apparatus for measuring a property of a material, comprising:
(a) a neutron source;
(b) a first gamma ray spectrometer displaced from said source at a first axial spacing and which measures a first gamma ray spectrum resulting from gamma radiation induced within said material by said neutron source;
(c) a second gamma ray spectrometer displaced from said source at a second axial spacing and which measures a second gamma ray spectrum resulting from said gamma radiation induced within said material by said neutron source; and
(d) a processor for
(i) normalizing said second gamma ray spectrum to said first gamma ray spectrum in a first energy region thereby creating a normalized second gamma ray spectrum, and
(ii) combining said first gamma ray spectrum with said normalized second gamma ray spectrum in a second energy region to determine a measure of said property.

19. The apparatus of claim 18 wherein said property is bulk density.

20. The apparatus of claim 18 wherein said induced gamma radiation comprises energies greater than about 3 MeV.

21. The apparatus of claim 18 wherein said second spacing is greater than said first spacing.

22. The apparatus of claim 18 wherein:
(a) said first energy region ranges from about 3 MeV to about 7 MeV;
(b) said second energy region ranges from about several hundred keV to about 3 MeV; and
(c) said first gamma ray spectrum in said second energy region is subtracted from said normalized second gamma ray spectrum in said second energy region to determine said measure of said property.

23. The apparatus of claim 18 wherein said neutron source comprises Californium-252.

24. The apparatus of claim 18 wherein said material is earth formation penetrated by a borehole.

25. The apparatus of claim 24 comprising means for conveyance along said borehole by a wireline.

26. The apparatus of claim 24 comprising means for conveyance along said borehole a drill string.

27. A method for determining bulk density of an earth formation penetrated by a borehole, the method comprising the steps of:
  (a) inducing gamma radiation within said formation by means of a neutron source;
  (b) measuring gamma ray counts resulting from said induced gamma radiation in a low energy window extending from about several hundred keV to about 3 MeV at a first axial spacing from said neutron source;
  (c) measuring gamma ray counts resulting from said induced gamma radiation in a high energy window extending from about 3 MeV to above 7 MeV at said first axial spacing;
  (d) measuring gamma ray counts resulting from said induced gamma radiation in said low energy window at a second axial spacing from said neutron source, wherein said second spacing is greater than said first axial spacing;
  (e) measuring gamma ray counts resulting from said induced gamma radiation in said high energy window at said second axial spacing;
  (f) computing a normalization factor by dividing said gamma ray counts measured at said first spacing in said high energy window by said gamma ray counts measured at said second axial spacing in said high energy window;
  (g) computing a normalized gamma ray count for said low energy window at said second axial spacing by multiplying said normalization factor by said gamma ray counts measured in said low energy window at said second axial spacing;
  (h) computing a low energy window count difference by subtracting said gamma ray count measured at said first axial spacing in said low energy window from said normalized gamma ray count;
  (i) correcting said low energy window count difference for effects of formation lithology to form a corrected low energy window count difference; and
  (j) determining said bulk density from said lithology corrected low energy window count difference using a predetermined functional relationship.

28. An apparatus for determining bulk density of an earth formation penetrated by a borehole, the apparatus comprising:
  (a) a Californium-252 neutron source which induces gamma radiation within said earth formation comprising energies ranging from about several hundred keV to about 10 MeV;
  (b) a short spaced gamma ray spectrometer displaced from said source at a first axial spacing and which responds to gamma radiation induced within said earth formation by said neutron source;
  (c) a long spaced gamma ray spectrometer displaced from said source at a second axial spacing and which responds to said gamma radiation induced within said earth formation by said neutron source, wherein said second axial spacing is greater than said first axial spacing; and
  (d) a processor which is preprogrammed to
    (i) store gamma ray counts detected by said short spaced spectrometer and resulting from said induced gamma radiation in a low energy window extending from about several hundred keV to about 3 MeV at a first axial spacing from said neutron source,
    (ii) store gamma ray counts detected by said short spaced spectrometer and resulting from said induced gamma radiation in a high energy window extending from about 3 MeV to above 7 MeV at said first axial spacing,
    (iii) store gamma ray counts detected by said long spaced spectrometer and resulting from said induced gamma radiation in said low energy window,
    (iv) store gamma ray counts detected by said long spaced spectrometer and resulting from said induced gamma radiation in said high energy window,
    (v) compute a normalization factor by dividing said gamma ray counts measured by said short spaced spectrometer in said high energy window by said gamma ray counts measured by said long spaced detector in said high energy window,
    (vi) compute a normalized gamma ray count for said low energy window in said long spaced spectrometer by multiplying said normalization factor by said gamma ray counts measured in said low energy window in said long spaced spectrometer,
    (vii) compute a low energy window count difference by subtracting said gamma ray count measured by said short spaced spectrometer in said low energy window from said normalized gamma ray count,
    (viii) correct said low energy window count difference for effects of formation lithology to form a corrected low window count difference, and
    (ix) determine said bulk density from said lithology corrected low energy window count difference using a predetermined functional relationship.

29. A method for determining bulk density of incident materials, the method comprising the steps of:
  (a) inducing gamma radiation within said material by means of a neutron source;
  (b) measuring gamma ray counts resulting from said induced gamma radiation in a low energy window extending from about several hundred keV to about 3 MeV at a first axial spacing from said neutron source;
  (c) measuring gamma ray counts resulting from said induced gamma radiation in a high energy window extending from about 3 MeV to above 7 MeV at said first axial spacing;
  (d) measuring gamma ray counts resulting from said induced gamma radiation in said low energy window at a second axial spacing from said neutron source, wherein said second spacing is greater than said first axial spacing;
  (e) measuring gamma ray counts resulting from said induced gamma radiation in said high energy window at said second axial spacing;
  (f) computing a normalization factor by dividing said gamma ray counts measured at said first spacing in said high energy window by said gamma ray counts measured at said second axial spacing in said high energy window;
  (g) computing a normalized gamma ray count for said low energy window at said second axial spacing by multiplying said normalization factor by said gamma ray counts measured in said low energy window at said second axial spacing;
  (h) computing a low energy window count difference by subtracting said gamma ray count measured at said first axial spacing in said low energy window from said normalized gamma ray count;
  (i) correcting said low energy window count difference for effects of the composition to form a corrected low energy window count difference; and
  (j) determining said bulk density from said corrected low energy window count difference using a predetermined functional relationship.

* * * * *